US011839426B2

(12) United States Patent
Brannan (10) Patent No.: US 11,839,426 B2
(45) Date of Patent: *Dec. 12, 2023

(54) MINIATURIZED MICROWAVE ABLATION ASSEMBLY (71) Applicant: Covidien LP, Mansfield, MA (US)

(72) Inventor: Joseph D. Brannan, Lyons, CO (US)

(73) Assignee: Covidien LP, Mansfield, MA (US)

( * ) Notice: Subject to any disclaimer, the term of this patent is extended or adjusted under 35 U.S.C. 154(b) by 614 days.

This patent is subject to a terminal disclaimer.

(21) Appl. No.: 17/034,011

(22) Filed: Sep. 28, 2020

(65) Prior Publication Data

US 2021/0077189 A1 Mar. 18, 2021

Related U.S. Application Data (63) Continuation of application No. 14/503,926, filed on Oct. 1, 2014, now Pat. No. 10,813,691.

(51) Int. Cl.
*A61B 18/18* (2006.01)
*A61B 18/00* (2006.01)

(52) U.S. Cl.
CPC *A61B 18/1815* (2013.01); *A61B 2018/00023* (2013.01); *A61B 2018/00577* (2013.01); *A61B 2018/1861* (2013.01)

(58) Field of Classification Search
CPC ...... A61B 18/1815; A61B 2018/00023; A61B 2018/00577; A61B 2018/1861
See application file for complete search history.

(56) References Cited

U.S. PATENT DOCUMENTS

D223,367 S 4/1972 Kountz
4,161,704 A 7/1979 Schafer
(Continued)

FOREIGN PATENT DOCUMENTS

CN 1103807 C 3/2003
CN 102570009 A 7/2012
(Continued)

OTHER PUBLICATIONS

IgaSureTM Vessel Sealing System, the Seal of Confidence in General, Gynecologic, Urologic, and Laparaoscopic Surgery, Sales/Product Literature, Jan. 2004.
(Continued)

*Primary Examiner* — Tigist S Demie
(74) *Attorney, Agent, or Firm* — Carter, DeLuca & Farrell LLP (57) ABSTRACT Microwave applicators are disclosed which include a first transmission line segment, a second transmission line segment, and a third transmission line segment. The first transmission line segment includes a first inner conductor, a first dielectric disposed on the first inner conductor, and a first outer conductor disposed on the first dielectric. The second transmission line segment includes a second inner conductor, a second dielectric disposed on the second inner conductor, and a second outer conductor disposed on the second dielectric. The third transmission line segment includes a third inner conductor disposed on the third inner conductor, a third outer conductor disposed on the proximal end of the third dielectric. The impedance of the second transmission line segment can be adjusted by adjusting the length of the third transmission line segment.

19 Claims, 6 Drawing Sheets

(56) References Cited

U.S. PATENT DOCUMENTS

| | | |
|---|---|---|
| D263,020 S | 2/1982 | Rau, III |
| D266,842 S | 11/1982 | Villers et al. |
| D278,306 S | 4/1985 | McIntosh |
| 4,583,589 A | 4/1986 | Kasevich |
| D295,893 S | 5/1988 | Sharkany et al. |
| D295,894 S | 5/1988 | Sharkany et al. |
| 5,301,687 A | 4/1994 | Wong et al. |
| 5,364,392 A | 11/1994 | Warner et al. |
| 5,370,644 A | 12/1994 | Langberg |
| 5,370,676 A | 12/1994 | Sozanski et al. |
| D354,218 S | 1/1995 | Van de Peer |
| 5,545,137 A | 8/1996 | Rudie et al. |
| 5,603,697 A | 2/1997 | Grundy et al. |
| 5,624,392 A | 4/1997 | Saab |
| 5,685,839 A | 11/1997 | Edwards et al. |
| 5,693,082 A | 12/1997 | Warner et al. |
| 5,741,249 A | 4/1998 | Moss et al. |
| 5,861,021 A | 1/1999 | Thome et al. |
| 5,980,505 A | 11/1999 | Wilson |
| 5,993,447 A | 11/1999 | Blewett et al. |
| 5,995,875 A | 11/1999 | Blewett et al. |
| 6,014,581 A | 1/2000 | Whayne et al. |
| D424,693 S | 5/2000 | Pruter |
| D424,694 S | 5/2000 | Tetzlaff et al. |
| D425,201 S | 5/2000 | Tetzlaff et al. |
| 6,061,551 A | 5/2000 | Sorrells et al. |
| 6,106,524 A | 8/2000 | Eggers et al. |
| 6,117,101 A | 9/2000 | Diederich et al. |
| 6,139,527 A | 10/2000 | Laufer et al. |
| 6,186,978 B1 | 2/2001 | Samson et al. |
| 6,210,367 B1 | 4/2001 | Carr |
| 6,222,500 B1 * | 4/2001 | Koitsalu ............... H01Q 19/09 333/33 |
| 6,235,024 B1 | 5/2001 | Tu |
| 6,277,113 B1 | 8/2001 | Berube |
| D449,886 S | 10/2001 | Tetzlaff et al. |
| 6,355,016 B1 | 3/2002 | Bagaoisan et al. |
| D457,958 S | 5/2002 | Dycus et al. |
| D457,959 S | 5/2002 | Tetzlaff et al. |
| 6,398,781 B1 | 6/2002 | Goble et al. |
| 6,427,089 B1 | 7/2002 | Knowlton |
| 6,485,486 B1 | 11/2002 | Trembly et al. |
| 6,496,737 B2 | 12/2002 | Rudie et al. |
| 6,496,738 B2 | 12/2002 | Carr |
| 6,514,249 B1 | 2/2003 | Maguire et al. |
| 6,547,788 B1 | 4/2003 | Maguire et al. |
| 6,575,969 B1 | 6/2003 | Rittman, III et al. |
| 6,599,288 B2 | 7/2003 | Maguire et al. |
| 6,629,974 B2 | 10/2003 | Penny et al. |
| 6,635,055 B1 | 10/2003 | Cronin |
| 6,652,515 B1 | 11/2003 | Maguire et al. |
| 6,676,657 B2 | 1/2004 | Wood |
| D487,039 S | 2/2004 | Webster et al. |
| 6,689,127 B1 | 2/2004 | Gough et al. |
| 6,706,040 B2 | 3/2004 | Mahon et al. |
| 6,723,091 B2 | 4/2004 | Goble et al. |
| 6,740,108 B1 | 5/2004 | Just et al. |
| 6,770,070 B1 | 8/2004 | Balbierz |
| 6,780,183 B2 | 8/2004 | Jimenez, Jr. et al. |
| D496,997 S | 10/2004 | Dycus et al. |
| D499,181 S | 11/2004 | Dycus et al. |
| 6,847,848 B2 | 1/2005 | Sterzer et al. |
| 6,869,431 B2 | 3/2005 | Maguire et al. |
| 6,893,436 B2 | 5/2005 | Woodard et al. |
| 6,932,776 B2 | 8/2005 | Carr |
| 6,997,925 B2 | 2/2006 | Maguire et al. |
| 7,004,938 B2 | 2/2006 | Ormsby et al. |
| 7,047,068 B2 | 5/2006 | Haissaguerre |
| 7,049,068 B2 | 5/2006 | Thorp et al. |
| D525,361 S | 7/2006 | Hushka |
| 7,089,063 B2 | 8/2006 | Lesh et al. |
| 7,113,832 B2 | 9/2006 | Longo |
| D531,311 S | 10/2006 | Guerra et al. |
| D533,942 S | 12/2006 | Kerr et al. |
| D535,027 S | 1/2007 | James et al. |
| 7,194,297 B2 | 3/2007 | Talpade et al. |
| 7,197,356 B2 | 3/2007 | Carr |
| D541,418 S | 4/2007 | Schechter et al. |
| 7,200,445 B1 | 4/2007 | Dalbec et al. |
| D541,938 S | 5/2007 | Kerr et al. |
| 7,261,001 B2 | 8/2007 | Heijnsdijk et al. |
| 7,263,398 B2 | 8/2007 | Carr |
| 7,275,547 B2 | 10/2007 | Willis |
| 7,285,116 B2 | 10/2007 | de la Rama et al. |
| 7,294,125 B2 | 11/2007 | Phalen et al. |
| 7,300,436 B2 | 11/2007 | Penny et al. |
| 7,303,558 B2 | 12/2007 | Swanson |
| D564,662 S | 3/2008 | Moses et al. |
| 7,402,168 B2 | 7/2008 | Sanderson et al. |
| 7,410,486 B2 | 8/2008 | Fuimaono et al. |
| D576,932 S | 9/2008 | Strehler |
| 7,438,712 B2 | 10/2008 | Chouinard |
| 7,460,898 B2 | 12/2008 | Brister et al. |
| 7,507,229 B2 | 3/2009 | Hewitt et al. |
| D594,736 S | 6/2009 | Esjunin |
| D594,737 S | 6/2009 | Kelly et al. |
| 7,608,056 B2 | 10/2009 | Kennedy, II |
| 7,611,508 B2 | 11/2009 | Yang et al. |
| D606,203 S | 12/2009 | Husheer et al. |
| D613,412 S | 4/2010 | DeCarlo |
| 7,697,972 B2 | 4/2010 | Verard et al. |
| 7,706,894 B2 | 4/2010 | Stewart et al. |
| 7,713,259 B2 | 5/2010 | Gosiengfiao et al. |
| 7,722,604 B2 | 5/2010 | Brown, III et al. |
| 7,734,330 B2 | 6/2010 | Carr |
| 7,769,469 B2 | 8/2010 | Carr et al. |
| 7,824,392 B2 | 11/2010 | Zhou |
| 7,826,904 B2 | 11/2010 | Appling et al. |
| 7,833,218 B2 | 11/2010 | Lunn et al. |
| D634,010 S | 3/2011 | DeCarlo |
| 7,921,855 B2 | 4/2011 | Danek et al. |
| 7,933,660 B2 | 4/2011 | Carr |
| 7,993,351 B2 | 8/2011 | Worley et al. |
| 8,021,351 B2 | 9/2011 | Boldenow et al. |
| 8,075,532 B2 | 12/2011 | Kassab et al. |
| 8,182,466 B2 | 5/2012 | Stehr et al. |
| 8,206,373 B2 | 6/2012 | Zhou |
| 8,206,380 B2 | 6/2012 | Lenihan et al. |
| 8,226,566 B2 | 7/2012 | Nita |
| 8,277,438 B2 | 10/2012 | Griffin et al. |
| 8,289,551 B2 | 10/2012 | Wu |
| 8,292,881 B2 | 10/2012 | Brannan et al. |
| 8,328,799 B2 | 12/2012 | Brannan |
| 8,328,800 B2 | 12/2012 | Brannan |
| 8,328,801 B2 | 12/2012 | Brannan |
| 8,340,740 B2 | 12/2012 | Holzer et al. |
| 8,343,145 B2 | 1/2013 | Brannan |
| 8,394,092 B2 | 3/2013 | Brannan |
| 8,412,306 B2 | 4/2013 | Kurpad et al. |
| D681,810 S | 5/2013 | DeCarlo |
| 8,515,554 B2 | 8/2013 | Carr |
| 8,574,227 B2 | 11/2013 | Hancock et al. |
| 8,655,454 B2 | 2/2014 | Prakash et al. |
| 8,672,932 B2 | 3/2014 | van der Weide et al. |
| 8,795,268 B2 | 8/2014 | Willyard |
| 9,526,568 B2 | 12/2016 | Ohri et al. |
| 9,814,844 B2 | 11/2017 | Ohri et al. |
| 10,813,691 B2 | 10/2020 | Brannan |
| 2002/0022836 A1 | 2/2002 | Goble et al. |
| 2002/0026187 A1 | 2/2002 | Swanson |
| 2003/0191451 A1 | 10/2003 | Gilmartin |
| 2004/0049254 A1 | 3/2004 | Longo |
| 2004/0243200 A1 | 12/2004 | Turner et al. |
| 2005/0176292 A1 | 8/2005 | Lee et al. |
| 2005/0215942 A1 | 9/2005 | Abrahamson et al. |
| 2005/0245920 A1 | 11/2005 | Vitullo et al. |
| 2006/0004351 A1 | 1/2006 | Arless et al. |
| 2006/0009833 A1 | 1/2006 | Chobotov et al. |
| 2006/0089637 A1 | 4/2006 | Werneth et al. |
| 2006/0167416 A1 | 7/2006 | Mathis et al. |
| 2006/0189973 A1 | 8/2006 | van der Weide |
| 2006/0241564 A1 | 10/2006 | Corcoran et al. |
| 2006/0253102 A1 | 11/2006 | Nance et al. |
| 2007/0088319 A1 | 4/2007 | Martone |

(56) References Cited

U.S. PATENT DOCUMENTS

| | | |
|---|---|---|
| 2007/0287912 A1 | 12/2007 | Khuri-Yakub et al. |
| 2008/0033424 A1 | 2/2008 | van der Weide et al. |
| 2008/0091169 A1 | 4/2008 | Heideman et al. |
| 2008/0147056 A1 | 6/2008 | van der Weide et al. |
| 2008/0208039 A1 | 8/2008 | Kurpad et al. |
| 2008/0228167 A1 | 9/2008 | Mittermeyer et al. |
| 2008/0255507 A1 | 10/2008 | Mushtaha |
| 2009/0076409 A1 | 3/2009 | Wu et al. |
| 2009/0187180 A1 | 7/2009 | Brannan |
| 2009/0222002 A1 | 9/2009 | Bonn et al. |
| 2009/0234220 A1 | 9/2009 | Maschke |
| 2010/0036369 A1 | 2/2010 | Hancock |
| 2010/0262134 A1 | 10/2010 | Jensen et al. |
| 2010/0268196 A1 | 10/2010 | Hastings et al. |
| 2010/0305559 A1 | 12/2010 | Brannan et al. |
| 2011/0004205 A1 | 1/2011 | Chu et al. |
| 2011/0118723 A1 | 5/2011 | Turner et al. |
| 2011/0130750 A1 | 6/2011 | Ormsby et al. |
| 2011/0166518 A1 | 7/2011 | Nguyen et al. |
| 2011/0166519 A1 | 7/2011 | Nguyen et al. |
| 2011/0282336 A1 | 11/2011 | Brannan et al. |
| 2011/0301587 A1 | 12/2011 | Deem et al. |
| 2012/0065481 A1 | 3/2012 | Hunter et al. |
| 2012/0071822 A1 | 3/2012 | Romo et al. |
| 2012/0078175 A1 | 3/2012 | Vreeman |
| 2012/0078230 A1 | 3/2012 | Lowe et al. |
| 2012/0172860 A1* | 7/2012 | Brannan ............ A61B 18/1815 606/33 |
| 2012/0232619 A1 | 9/2012 | Turovskiy et al. |
| 2012/0259326 A1 | 10/2012 | Brannan et al. |
| 2012/0277730 A1 | 11/2012 | Salahieh et al. |
| 2013/0137977 A1 | 5/2013 | Eder |
| 2013/0178841 A1 | 7/2013 | Reid, Jr. |
| 2013/0197481 A1 | 8/2013 | Guo et al. |
| 2013/0197482 A1 | 8/2013 | Akitomo |
| 2013/0237980 A1 | 9/2013 | Brannan |
| 2013/0241769 A1 | 9/2013 | Brannan et al. |
| 2013/0245624 A1 | 9/2013 | Bahney |
| 2013/0253500 A1 | 9/2013 | Lee et al. |
| 2013/0261617 A1 | 10/2013 | Podhajsky |
| 2013/0261620 A1 | 10/2013 | Brannan et al. |
| 2013/0267946 A1 | 10/2013 | Brannan et al. |
| 2013/0289560 A1 | 10/2013 | DeCarlo et al. |
| 2013/0296841 A1 | 11/2013 | Brannan |
| 2013/0304057 A1 | 11/2013 | Rossetto |
| 2013/0317407 A1 | 11/2013 | Reid, Jr. et al. |
| 2013/0317495 A1 | 11/2013 | Brannan |
| 2013/0317499 A1 | 11/2013 | Brannan et al. |
| 2013/0324910 A1 | 12/2013 | Ohri et al. |
| 2013/0324911 A1 | 12/2013 | Ohri et al. |
| 2013/0338661 A1 | 12/2013 | Behnke, II |
| 2013/0345541 A1 | 12/2013 | Nau, Jr. |
| 2013/0345551 A1 | 12/2013 | Arts et al. |
| 2013/0345552 A1 | 12/2013 | Arts et al. |
| 2013/0345553 A1 | 12/2013 | Arts et al. |
| 2013/0345699 A1 | 12/2013 | Brannan et al. |
| 2014/0000098 A1 | 1/2014 | Dunning et al. |
| 2014/0005655 A1 | 1/2014 | Brannan |
| 2014/0005657 A1 | 1/2014 | Brannan et al. |
| 2014/0018668 A1 | 1/2014 | Zheng et al. |
| 2014/0018677 A1 | 1/2014 | Sharonov |
| 2014/0018793 A1 | 1/2014 | Sharonov |
| 2014/0052125 A1 | 2/2014 | Bra et al. |
| 2014/0094789 A1 | 4/2014 | Brannan |
| 2014/0094792 A1 | 4/2014 | Sharonov |
| 2014/0094794 A1 | 4/2014 | Orszulak |
| 2014/0094797 A1 | 4/2014 | Brannan |
| 2014/0276739 A1 | 9/2014 | Brannan et al. |
| 2014/0290830 A1 | 10/2014 | Brannan |
| 2015/0022342 A1 | 1/2015 | Will et al. |

FOREIGN PATENT DOCUMENTS

| | | |
|---|---|---|
| CN | 102711643 A | 10/2012 |
| DE | 390937 C | 3/1924 |
| DE | 1099658 B | 2/1961 |
| DE | 1139927 B | 11/1962 |
| DE | 1149832 B | 6/1963 |
| DE | 1439302 A1 | 1/1969 |
| DE | 2439587 A1 | 2/1975 |
| DE | 2455174 A1 | 5/1975 |
| DE | 2407559 A1 | 8/1975 |
| DE | 2415263 A1 | 10/1975 |
| DE | 2429021 A1 | 1/1976 |
| DE | 2460481 A1 | 6/1976 |
| DE | 2602517 A1 | 7/1976 |
| DE | 2504280 A1 | 8/1976 |
| DE | 2627679 A1 | 1/1977 |
| DE | 2540968 A1 | 3/1977 |
| DE | 2820908 A1 | 11/1978 |
| DE | 2803275 A1 | 8/1979 |
| DE | 2823291 A1 | 11/1979 |
| DE | 2946728 A1 | 5/1981 |
| DE | 3143421 A1 | 5/1982 |
| DE | 3045996 A1 | 7/1982 |
| DE | 3120102 A1 | 12/1982 |
| DE | 3510586 A1 | 10/1986 |
| DE | 3604823 A1 | 8/1987 |
| DE | 3712328 U1 | 2/1988 |
| DE | 3711511 C1 | 6/1988 |
| DE | 3904558 A1 | 8/1990 |
| DE | 3942998 A1 | 7/1991 |
| DE | 4238263 A1 | 5/1993 |
| DE | 04303882 C2 | 2/1995 |
| DE | 4339049 A1 | 5/1995 |
| DE | 29616210 U1 | 11/1996 |
| DE | 19608716 C1 | 4/1997 |
| DE | 19751106 A1 | 5/1998 |
| DE | 19717411 A1 | 11/1998 |
| DE | 19751108 A1 | 5/1999 |
| DE | 19801173 C1 | 7/1999 |
| DE | 19848540 A1 | 5/2000 |
| DE | 10224154 A1 | 12/2003 |
| DE | 10310765 A1 | 9/2004 |
| DE | 10328514 B3 | 3/2005 |
| DE | 102004022206 A1 | 12/2005 |
| DE | 202005015147 U1 | 2/2006 |
| DE | 102009015699 A1 | 5/2010 |
| EP | 0246350 A1 | 11/1987 |
| EP | 0521264 A2 | 1/1993 |
| EP | 0556705 A1 | 8/1993 |
| EP | 0558429 A1 | 9/1993 |
| EP | 0648515 A1 | 4/1995 |
| EP | 0836868 A2 | 4/1998 |
| EP | 0882955 A1 | 12/1998 |
| EP | 1034747 A1 | 9/2000 |
| EP | 1034748 A1 | 9/2000 |
| EP | 1055400 A1 | 11/2000 |
| EP | 1159926 A2 | 3/2003 |
| EP | 2147651 A1 | 1/2010 |
| EP | 2322113 A1 | 5/2011 |
| FR | 179 607 | 11/1906 |
| FR | 1275415 A | 11/1961 |
| FR | 1347865 A | 1/1964 |
| FR | 2 235 669 A1 | 1/1975 |
| FR | 2 276 027 A1 | 1/1976 |
| FR | 2313708 A1 | 12/1976 |
| FR | 2502935 A1 | 10/1982 |
| FR | 2517953 A1 | 6/1983 |
| FR | 2573301 A1 | 5/1986 |
| FR | 2 862 813 A1 | 5/2005 |
| FR | 2 864 439 A1 | 7/2005 |
| JP | 55106 | 1/1993 |
| JP | 0540112 | 2/1993 |
| JP | 06343644 | 12/1994 |
| JP | 07265328 | 10/1995 |
| JP | 08056955 | 3/1996 |
| JP | 08252263 A | 10/1996 |
| JP | 09000492 A | 1/1997 |
| JP | 09010223 | 1/1997 |

(56) References Cited

FOREIGN PATENT DOCUMENTS

| | | |
|---|---|---|
| JP | 11244298 | 9/1999 |
| JP | 2000342599 A | 12/2000 |
| JP | 2000350732 A | 12/2000 |
| JP | 2001003776 A | 1/2001 |
| JP | 2001008944 | 1/2001 |
| JP | 2001029356 | 2/2001 |
| JP | 2001037775 | 2/2001 |
| JP | 2001128990 A | 5/2001 |
| JP | 2001231870 A | 8/2001 |
| JP | 2008142467 A | 6/2008 |
| JP | 2013511348 A | 4/2013 |
| KR | 20070093068 A | 9/2007 |
| KR | 20100014406 A | 2/2010 |
| KR | 20120055063 A | 5/2012 |
| SU | 166452 | 11/1964 |
| SU | 401367 A1 | 10/1973 |
| SU | 727201 A2 | 4/1980 |
| WO | 9416632 A1 | 8/1994 |
| WO | 9724074 A1 | 7/1997 |
| WO | 0036985 A2 | 6/2000 |
| WO | 0057811 A1 | 10/2000 |
| WO | 0100114 A1 | 1/2001 |
| WO | 02/45790 A2 | 6/2002 |
| WO | 2008068485 A2 | 6/2008 |
| WO | 2010035831 A1 | 4/2010 |
| WO | 2014025551 A1 | 2/2014 |
| WO | 2014160931 A1 | 10/2014 |

OTHER PUBLICATIONS

Livraghi et al., (1995) "Saline-enhanced RF Tissue Ablation in the Treatment of Liver Metastases", Radiology, p. 140 (Abstr).

Lyndon B. Johnson Space Center, Houston, Texas, "Compact Directional Microwave Antenna for Localized Heating," NASA Tech Briefs, Mar. 2008.

M. A. Astrahan, "A Localized Current Field Hyperthermia System for Use with 192-Iridium Interstitial Implants" Medical Physics. 9(3), May-Jun. 1982.

Magdy F. Iskander et al., "Design Optimization of Interstitial Antennas", IEEE Transactions on Biomedical Engineering, vol. 36, No. 2, Feb. 1989, pp. 238-246.

McGahan et al., (1995) "Percutaneous Ultrasound-guided Radiofrequency Electrocautery Ablation of Prostate Tissue in Dogs", Acad Radiol, vol. 2, No. 1: pp. 61-65.

McLellan et al., "Vessel Sealing for Hemostasis During Pelvic Surgery" Int'l Federation of Gynecology and Obstetrics Figo World Congress 2000, Washington, DC.

MDTECH product literature (Dec. 1999) "FlexStrand": product description, 1 page.

MDTECH product literature (Mar. 2000) I'D Wire: product description, 1 page.

Medtrex Brochure "The O.R. Pro 300" 1 page; Sep. 1998.

Michael Choti, "Abdominoperineal Resection with the LigaSureTM Vessel Sealing System and LigaSureTM Atlas 20 cm Open Instrument" Innovations That Work, Jun. 2003.

Muller et al., "Extended Left Hemicolectomy Using the LigaSureTM Vessel Sealing System" Innovations That Work. LJ, Sep. 1999.

Murakami, R. et al., (1995). "Treatment of Hepatocellular Carcinoma: Value of Percutaneous Microwave Coagulation," American Journal of Radiology (AJR) 164:1159-1164.

Ni Wei et al., "A Signal Processing Method for the Coriolis Mass Flowmeter Based on a Normalized . . . " Journal of Applied Sciences Yingyong Kexue Xuebao, Shangha CN, vol. 23, No. 2:(Mar. 2005); pp. 160-184.

Ogden, "Goertzel Alternative to the Fourier Transform": Jun. 1993 pp. 485-487 Electronics World; Reed Business Publishing, Sutton, Surrey, BG, vol. 99, No. 9, 1687.

Olsson M.D. et al., "Radical Cystectomy in Females" Current Surgical Techniques in Urology, vol. 14, Issue 3, 2001.

Organ, L W., "Electrophysiologic Principles of Radiofrequency Lesion Making" Appl. Neurophysiol, vol. 39: pp. 69-76 (1976/77).

P.R. Stauffer et al., "Interstitial Heating Technologies", Thermoradiotheray and Thermochemotherapy (1995) vol. I, Biology, Physiology, Physics, pp. 279-320.

Palazzo et al., "Randomized clinical trial of LigaSureTM versus open haemorrhoidectomy" British Journal of Surgery 2002, 89, 154-157 "Innovations in Electrosurgery" Sales/Product Literature; Dec. 31, 2000.

Paul G. Horgan, "A Novel Technique for Parenchymal Division During Hepatectomy" The American Journal of Surgery, vol. 181, No. 3, Apr. 2001 pp. 236-237.

Peterson et al., "Comparison of Healing Process Following Ligation with Sutures and Bipolar Vessel Sealing" Surgical Technology International (2001).

R. Gennari et al., (Jun. 2000) "Use of Technetium-99m-Labeled Colloid Albumin for Preoperative and Intraoperative Localization of Non palpable Breast Lesions," American College of Surgeons. 190(6):692-699.

Valleylab Brochure. "Reducing Needlestick Injuries in the Operating Room" 1 page, Mar. 2001.

Reidenbach, (1995) "First Experimental Results with Special Applicators for High-Frequency Interstitial Thermotherapy", Society Minimally Invasive Therapy, 4(Suppl 1):40 (Abstr).

Richard Wolf Medical Instruments Corp. Brochure, "Kleppinger Bipolar Forceps & Bipolar Generator" 3 pages, Jan. 1989.

Rothenberg et al., "Use of the LigaSureTM Vessel Sealing System in Minimally Invasive Surgery in Children" Int'L Pediatric Endosurgery Group (I PEG) 2000.

Sayfan et al., "Sutureless Closed Hemorrhoidectomy: A New Technique" Annals of Surgery, vol. 234, No. 1, Jul. 2001, pp. 21-24.

Sengupta et al., "Use of a Computer-Controlled Bipolar Diathermy System in Radical Prostatectomies and Other Open Urological Surgery" ANZ Journal of Surgery (2001)71.9 pp. 538-540.

Sigel et al., "The Mechanism of Blood Vessel Closure by High Frequency Electrocoagulation" Surgery Gynecology & Obstetrics, Oct. 1965 pp. 823-831.

Solbiati et al., (2001) "Percutaneous Radio-frequency Ablation of Hepatic Metastases from Colorectal Cancer: Long-term Results in 117 Patients", Radiology, vol. 221, pp. 159-166.

Solbiati et al. (1995) "Percutaneous US-guided RF Tissue Ablation of Liver Metastases: Long-term Follow-up", Radiology, pp. 195-203.

Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.

Sugita et al., "Bipolar Coagulator with Automatic Thermocontrol" J. Neurosurg., vol. 41, Dec. 1944, pp. 777-779.

Sylvain Labonte et al., "Monopole Antennas for Microwave Catheter Ablation", IEEE Trans. on Microwave Theory and Techniques, vol. 44, No. 10, pp. 1832-1840, Oct. 1995.

T. Matsukawa et al., "Percutaneous Microwave Coagulation Therapy in Liver Tumors", Acta Radiologica, vol. 38, pp. 410-415, 1997.

T. Seki et al., (1994) "Ultrasonically Guided Percutaneous Microwave Coagulation Therapy for Small Hepatocellular Carcinoma," Cancer 74(3):817-825.

Urologix, Inc .—Medical Professionals: TargisTM Technology (Date Unknown). "Overcoming the Challenge" located at: <http://www.urologix.com!medicaUtechnology.html > Nov. 18, 1999; 3 pages.

Urrutia et al., (1988). "Retractable-Barb Needle for Breast Lesion Localization: Use in 60 Cases," Radiology 169(3):845-847.

Valleylab Brochure, "Valleylab Electroshield Monitoring System" 2 pages, Nov. 1995.

ValleyLab Brochure, "Electosurgery: A Historical Overview", Innovations in Electrosurgery, 1999.

Vallfors et al., "Automatically Controlled Bipolar Electrocoagulation—'COA-COMP" Neurosurgical Review 7:2-3 (1984) pp. 187-190.

W. Scott Helton, "LigaSureTM Vessel Sealing System: Revolutionary Hemostasis Product for General Surgery" Sales/Product Literature 1999.

Wald et al., "Accidental Burns", JAMA, Aug. 16, 1971, vol. 217, No. 7, pp. 916-921.

(56) References Cited

OTHER PUBLICATIONS

Walt Boyles, "Instrumentation Reference Book", 2002, Butterworth-Heinemann, pp. 262-264.
Wonnell et al., "Evaluation of Microwave and Radio Frequency Catheter Ablation in a Myocardium-Equivalent Phantom Model", IEEE Transactions on Biomedical Engineering, vol. 39, No. 10, Oct. 1992; pp. 1086-1095.
U.S. Appl. No. 08/136,098, filed Oct. 14, 1993, Roger A. Stern.
U.S. Appl. No. 08/483,742, filed Jun. 7, 1995, Roger A. Stemn.
Alexander et al., "Magnetic Resonance Image-Directed Stereotactic Neurosurgery: Use of Image Fusion with Computerized Tomography to Enhance Spatial Accuracy", Journal Neurosurgery, 83; (1995) pp. 271-276.
Anderson et al., "A Numerical Study of Rapid Heating for High Temperature Radio Frequency Hyperthermia" International Journal of Bio-Medical Computing, 35 (1994), pp. 297-307.
Anonymous. (1999) Auto Suture MIBB Site Marker: Single Use Clip Applier, United States Surgical (Product Instructions), 2 pages.
Chinese Office Action for application No. 201580053360.0 dated Dec. 5, 2018 with English translation, 20 pages.
Chinese Office Action issued in Chinese Patent Application No. 201580053360.0 dated Jul. 22, 2019 with English translation.
Australian Examination Report for application No. 2015325120 dated Jun. 12, 2019.
Japanese Office Action for Application No. 2017-517323 dated Aug. 23, 2019 with English Translation.
Anonymous. (2001) Disposable Chiba Biopsy Needles and Trays, Biopsy and Special Purpose Needles Cook Diagnostic and Interventional Products Catalog (products list), 4 pages.
Anonymous. (1987) Homer Mammalok. TM. Breast Lesion Needle/Wire Localizer, Namic.RTM. Angiographic Systems Division, Glens Falls, New York, (Hospital products price list), 4 pages.
Anonymous. (1999) MIBB Site Marker, United States Surgical (Sales brochure), 4 pages.
Anonymous. Blunt Tubes with Finished Ends. Pointed Cannula, Popper & Sons Biomedical Instrument Division. (Products Price List), one page, Jul. 19, 2000.
Anonymous. Ground Cannulae, ISPG, New Milford, CT, (Advertisement) one page, Jul. 19, 2000.
B. Levy M.D. et al., "Randomized Trial of Suture Versus Electrosurgical Bipolar Vessel Sealing in Vaginal Hysterectomy" Obstetrics & Gynecology. vol. 102, No. 1, Jul. 2003.
B. Levy M.D. et al., "Update on Hysterectomy New Technologies and Techniques" OBG Management. Feb. 2003.
B. Levy M.D.. "Use of a New Vessel Ligation Device During Vaginal Hysterectomy" FIGO 2000, Washington, D.C.
B. F. Mullan et al., (May 1999) "Lung Nodules: Improved Wire for CT-Guided Localization," Radiology 211:561-565.
B. T. Heniford M.D. et al., "Initial Research and Clinical Results with an Electrothermal Bipolar Vessel Sealer" Oct. 1999.
Bergdahl et al., "Studies on Coagulation and the Development of an Automatic Computerized Bipolar Coagulator" Journal of Neurosurgery 75:1, (Jul. 1991) pp. 148-151.
Bulletin of the American Physical Society, vol. 47, No. 5, Aug. 2002, p. 41.
C. F. Gottlieb et al., "Interstitial Microwave Hyperthermia Applicators having Submillimetre Diameters", Int. J. Hyperthermia, vol. 6, No. 3, pp. 707-714, 1990.
C. H. Durney et al.. "Antennas for Medical Applications", Antenna Handbook: Theory Application and Design, p. 24-40. Van Nostrand Reinhold, 1988 New York, V.T. Lo, S.W. Lee.
Carbonell et al., "Comparison of the Gyrus PlasmaKinetic Sealer and the Valleylab LigaSure. TM. Device in the Hemostasis of Small, Medium, and Large-Sized Arteries" Carolinas Laparoscopic and Advanced Surgery Program, Carolinas MedicalCenter, Charlotte, NC 2003.
Carus et al., "Initial Experience With the LigaSure. TM. Vessel Sealing System in Abdominal Surgery" Innovations That Work, Jun. 2002.
Chicharo et al., "A Sliding Goertzel Algorithm" Aug. 1996 DOS pp. 283-297 Signal Processing, Elsevier Science Publishers B.V. Amsterdam, NL, vol. 52. No. 3.
Chou, C.K., (1995) "Radiofrequency Hyperthermia in Cancer Therapy," Chapter 941n Biologic Effects of Nonionizing Electromagnetic Fields, CRC Press, Inc., pp. 1424-1428.
Chung et al., "Clinical Experience of Sutureless Closed Hemorrhoidectomy with LigaSureTM" Diseases of the Colon & Rectum, vol. 46, No. 1, Jan. 2003.
Cosman et al., "Methods of Making Nervous System Lesions", In William RH, Rengachary SS (eds): Neurosurgery, New York: McGraw-Hill, vol. 111, (1984), pp. 2490-2499.
Cosman et al., "Radiofrequency Lesion Generation and its Effect on Tissue Impedence", Applied Neurophysiology, 51:230-242, 1988.
Cosman et al., "Theoretical Aspects of Radiofrequency Lesions in the Dorsal Root Entry Zone", Neurosurgery 15: (1984) pp. 945-950.
Crawford et al., "Use of the LigaSure. TM. Vessel Sealing System in Urologic Cancer Surger" Grand Rounds in Urology 1999, vol. 1, Issue 4, pp. 10-17.
Dulemba et al. "Use of a Bipolar Electrothermal Vessel Sealer in Laparoscopically Assisted Vaginal Hysterectomy" Sales/Product Literature; Jan. 2004.
E. David Crawford, "Evaluation of a New Vessel Sealing Device in Urologic Cancer Surgery" Sales/Product Literature 2000.
E. David Crawford, "Use of a Novel Vessel Sealing Technology in Management of the Dorsal Veinous Complex" Sales/Product Literature 2000.
Esterline, "Light Key Projection Keyboard" Advanced Input Systems, located at: <http://www.advanced-input.com/lightkey> 2002.
Esterline Product Literature, "Light Key: Visualize a Virtual Keyboard. One With No Moving Parts". Nov. 1, 2003; 4 pages.
Geddes et al.. "The Measurement of Physiologic Events by Electrical Impedence" Am. J. MI, Jan. Mar. 1964, pp. 16-27.
Goldberg et al., "Image-guided Radiofrequency Tumor Ablation: Challenges and Opportunities—Part I", (2001) J Vasc. Interv. Radio, vol. 12, pp. 1021-1032.
Goldberg et al. (1995) "Saline-enhanced RF Ablation: Demonstration of Efficacy and Optimization of Parameters", Radiology, 197(P): 140 (Abstr).
Goldberg et al., "Tissue Ablation with Radiofrequency: Effect of Probe Size, Gauge, Duration, and Temperature on Lesion Volume" Acad Radio (1995) vol. 2, No. 5, pp. 399-404.
H. Schwarzmaier et al., "Magnetic Resonance Imaging of Microwave Induced Tissue Heating" Dept. of Laser Medicine & Dept. of Diagnostic Radiology; Heinrich-Heine-University, Duesseldorf Germany; Dec. 8, 1994; pp. 729-731.
Teniford et al., "Initial Results with an Electrothermal Bipolar Vessel Sealer" Surgical Endoscopy (2001) 15:799-801.
Herman at al., "Laparoscopic Intestinal Resection With the LigaSureTM Vessel Sealing System: A Case Report" Innovations That Work, Feb. 2002.
Humphries Jr. et al., "Finite-Element Codes to Model Electrical Heating and Non-Linear Thermal Transport in Biological Media", Proc. ASME HTD-355, 131 (1997).
Ian D. McRury et al., The Effect of Ablation Sequence and Duration on Lesion Shape Using Rapidly Pulsed Radiofrequency Energy Through Electrodes, Feb. 2000, Springer Netherlands. vol. 4; No. 1. pp. 307-320.
Jarrett et al., "Use of the LigaSureTM Vessel Sealing System for Peri-Hilar Vessels in Laparoscopic Nephrectomy" Sales/Product Literature 2000.
Johnson et al. "Evaluation of a Bipolar Electrothermal Vessel Sealing Device in Hemorrhoidectomy" Sales/Product Literature; Jan. 2004.
Johnson, "Evaluation of the LigaSureTM Vessel Sealing System in Hemorrhoidectormy" American College of Surgeons (ACS) Clinic La Congress Poster (2000).
Johnson et al., "New Low-Profile Applicators for Local Heating of Tissues", IEEE Transactions on Biomedical Engineering, vol. BME-31, No. 1, Jan. 1984, pp. 28-37.
Johnson, "Use of the LigaSureTM Vessel Sealing System in Bloodless Hemorrhoidectomy" Innovations That Work, Mar. 2000.

(56) References Cited

OTHER PUBLICATIONS

Joseph G. Andriole, M.D., et al., "Biopsy Needle Characteristics Assessed in the Laboratory", Radiology 148: 659-662, Sep. 1983.
Joseph Ortenberg, "LigaSureTM System Used in Laparoscopic 1st and 2nd Stage Orchiopexy" Innovations That Work, Nov. 2002.
Kennedy et al. "High-burst-strength, feedback-controlled bipolar vessel sealing" Surgical Endoscopy (1998) 12:876-878.
Kopans, D.B. et al., (Nov. 1985) "Spring Hookwire Breast Lesion Localizer: Use with Rigid-Compression. Mammographic Systems," Radiology 157(2):537-538.
Koyle et al., "Laparoscopic Palomo Varicocele Ligation in Children and Adolescents" Pediatric Endosurgery & Innovative Techniques, vol. 6, No. 1, 2002.
International Search Report and Written Opinion for International Patent Application No. PCT/US2015/053134, dated Jan. 8, 2016.
Partial Supplementary European Search Report issued in corresponding application No. 15846381.0 dated Sep. 25, 2018, 11 pages.
European Search report for application No. 15 84 6381 dated Jan. 22, 2019.

\* cited by examiner

MINIATURIZED MICROWAVE ABLATION ASSEMBLY

CROSS-REFERENCE TO RELATED APPLICATIONS

This application is a continuation of U.S. patent application Ser. No. 14/503,926, filed on Oct. 1, 2014.

INTRODUCTION

The present disclosure relates generally to microwave ablation assemblies, and, more particularly, to miniaturized microwave ablation assemblies and maximizing their power transfer.

BACKGROUND

Electromagnetic fields can be used to heat and destroy tumor cells. Treatment may involve inserting ablation probes into tissues where cancerous tumors have been identified. Once the ablation probes are properly positioned, the ablation probes induce electromagnetic fields within the tissue surrounding the ablation probes.

In the treatment of diseases such as cancer, certain types of tumor cells have been found to denature at elevated temperatures that are slightly lower than temperatures normally injurious to healthy cells. Known treatment methods, such as hyperthermia therapy, heat diseased cells to temperatures above 41° C. while maintaining adjacent healthy cells below the temperature at which irreversible cell destruction occurs. These methods involve applying electromagnetic fields to heat or ablate tissue.

Devices utilizing electromagnetic fields have been developed for a variety of uses and applications. Typically, apparatuses for use in ablation procedures include a power generation source, e.g., a microwave generator that functions as an energy source, and a surgical instrument (e.g., microwave ablation probe having an antenna assembly) for directing energy to the target tissue. The generator and surgical instrument are typically operatively coupled by a cable assembly having a plurality of conductors for transmitting energy from the generator to the instrument, and for communicating control, feedback, and identification signals between the instrument and the generator.

There are several types of microwave probes in use, e.g., monopole, dipole, and helical, which may be used in tissue ablation applications. In monopole and dipole antenna assemblies, microwave energy generally radiates perpendicularly away from the axis of the conductor. Monopole antenna assemblies typically include a single, elongated conductor. A typical dipole antenna assembly includes two elongated conductors that are linearly-aligned and positioned end-to-end relative to one another with an electrical insulator placed therebetween. Helical antenna assemblies include helically-shaped conductor configurations of various dimensions, e.g., diameter and length. The main modes of operation of a helical antenna assembly are normal mode (broadside), in which the field radiated by the helix is maximum in a perpendicular plane to the helix axis, and axial mode (end fire), in which maximum radiation is along the helix axis.

The heating of tissue for thermal ablation is accomplished through a variety of approaches, including conduction of heat from an applied surface or element, ionic agitation by electrical current flowing from an electrode to a ground pad, optical wavelength absorption, or, in the case of microwave ablation, by dielectric relaxation of water molecules within an antenna electromagnetic field. The ablation zone can be broken down into two components: an active ablation zone and a passive ablation zone.

The active ablation zone is closest to the ablation device and encompasses the volume of tissue which is subjected to energy absorption high enough to assure thermal tissue destruction at a given application time in all but areas of very rapidly flowing fluids, such as around and within large blood vessels or airways. The active ablation zone size and shape is determined by ablation device design. The active ablation zone can therefore be used to produce predictable ablative effects over a given shape and volume of tissue.

The passive ablation zone surrounds the active zone and encompasses the volume of tissue which experiences a lower intensity of energy absorption. The tissue within the passive ablation zone may or may not experience tissue destruction at a given application time. Physiological cooling may counter heating from the lower level energy absorption and therefore not allow for sufficient heating to occur within the passive zone to kill tissue. Diseased or poorly perfused tissue within the passive zone may be more prone to heating than other tissues and may also be more susceptible to heat conduction from hotter areas within the ablation zone. The passive zone in these cases can result in unexpectedly large ablation zones. Due to these varying scenarios across space within a targeted physiology, relying on the passive zone to perform thermal ablation is challenging with unpredictable outcomes.

As electromagnetic fields can be induced at a distance by microwave probes, microwave ablation has the potential to create large active zones whose shapes can be determined and held constant by design. Furthermore, the shape and size can be determined through design to fit a specific medical application. By utilizing a predetermined active zone to create a predictable ablation zone, and not relying upon the indeterminate passive ablation zone, microwave ablation can provide a level of predictability and procedural relevance not possible with other ablative techniques.

The shape of the active zone about an antenna is determined by the frequency of operation, the geometry of the antenna, the materials of the antenna, and the medium surrounding the antenna. Operating an antenna in a medium of dynamically changing electrical properties, such as heating tissue, results in a changing shape of the electromagnetic field, and therefore a changing shape of the active zone. To maintain the shape of the active zone about a microwave antenna, the degree of influence on the electromagnetic field of the surrounding medium's electrical properties are reduced.

The size of the active zone about an antenna is determined by the amount of energy which can be delivered from the microwave generator to the antenna. With more energy delivered to the antenna, larger active zones can be generated. To maximize energy transfer from a microwave generator through waveguides and to a microwave antenna requires each system component to have the same impedance, or to be impedance matched. Whereas the impedance of the generator and waveguides are typically fixed, the impedance of a microwave antenna is determined by the frequency of operation, the geometry of the antenna, the materials of the antenna, and the medium surrounding the antenna. Operating an antenna in a medium of dynamically changing electrical properties, such as within heating tissue, results in a changing antenna impedance and varied energy delivery to the antenna, and, as a result, a changing size of the active zone. To maintain the size of the active zone about a microwave antenna, the degree of influence on the antenna impedance of the surrounding medium's electrical properties must be reduced.

In thermal ablation, the primary cause of active zone size and shape change is an elongation of the electromagnetic wave. Wavelength elongation occurs in heating tissue due to tissue dehydration. Dehydration reduces the dielectric constant, elongating the wavelength of microwave fields. Wavelength elongation is also encountered when a microwave device is used across various tissue types due to the varying dielectric constant between tissue types. For example, an electromagnetic wave is significantly longer in lung tissue than in liver tissue.

Wavelength elongation compromises the focus of microwave energy on the targeted tissue. With large volume ablation, a generally spherical active zone is preferable to focus the energy on generally spherical tissue targets. Wavelength elongation causes the electromagnetic field to stretch down along the length of the device toward the generator, resulting in a generally comet- or "hot-dog"-shaped active zone.

Wavelength elongation can be significantly reduced in medical microwave antennas by dielectrically buffering the antenna geometry with a material having an unchanging dielectric constant, as described in U.S. application Ser. Nos. 13/835,283 and 13/836,519, the disclosure of each of which are incorporated by reference herein. The material of unchanging dielectric constant surrounds the antenna, reducing the influence of the tissue electrical properties on antenna wavelength. By controlling wavelength elongation through dielectric buffering, the antenna impedance match and field shape can be maintained, enabling a large active ablation zone with a predetermined and robust shape.

By providing dielectric buffering with a circulated fluid, such as with saline or water, the high dielectric constants of these materials can be leveraged in the antenna geometry design, and furthermore the circulated fluid can be used to simultaneously cool the microwave components, including the coaxial feed line and antenna. Cooling of the microwave components also enables higher power handling of the components which can be used to deliver more energy to the antenna to create larger active zones.

As described above, the shape of the active zone about an antenna is determined, in part, by the geometry of the antenna. Ordinary ablation antennas do not utilize antenna geometry in combination with wavelength buffering to effectively control microwave field shape. These antennas do not create spherical active zone shapes nor are the active zones robust and unchanging across tissue types or during tissue heating. These antennas allow microwave energy to spread along the external conductor of the device from the device tip towards the generator. The spreading of microwave energy along the shaft results in comet- or "hot-dog"-shaped active zones.

Microwave antennas can be equipped with a choke or balun, a component of the antenna geometry that improves impedance matching and also can aid in focusing microwave energy into a predetermined shape. When combined with wavelength buffering, a balun or choke can effectively block the backwards propagation of electromagnetic waves along the external conductor toward the generator across various tissue types and during tissue heating, focusing the energy into a robust spherical active zone.

One implementation of a balun includes a balun dielectric that is disposed on the outer conductor of a coaxial cable and an outer balun conductor disposed on the balun dielectric. The balun creates a short section of coaxial waveguide arranged about the inner coaxial cable where the outer conductor of the coaxial cable is the inner conductor of the balun. The balun is disposed about the coaxial cable near the feed of the antenna and in one implementation has a length of $\lambda/4$ where $\lambda$ is the wavelength of the electromagnetic wave within the balun. The balun outer conductor and inner conductors are shorted together at the proximal end to create a $\lambda/4$ short-circuited balun.

One way of describing the function of a $\lambda/4$ short-circuited balun is as follows: an electromagnetic wave propagates proximally along the radiating section of the antenna, enters the balun, reflects off of the short-circuited proximal end of the balun, propagates forward to the distal end of the balun, and exits the balun back onto the antenna radiating section. With this arrangement of balun length, when the electromagnetic wave reaches the distal end of the balun and travels back onto the antenna radiating section, the electromagnetic wave has accumulated a full $\lambda$ of phase change. This is due to the $\lambda/4$ distance traveled forward within the balun, the $\lambda/4$ distance traveled backward within the balun and a $\lambda/2$ phase change which occurs with the reflection off of the short-circuited proximal end of the balun. The result is an electromagnetic wave which, rather than propagating along the external surface of the cable toward the generator, is a wave which is redirected back toward the distal tip of the antenna in coherent phase with the other waves on the antenna radiating section.

Because of the various components needed in the microwave ablation assembly, the diameter of the microwave ablation assembly is increased as well as the needle through which the microwave ablation assembly passes. The size of the needle may limit the uses for the microwave ablation assembly in minimally-invasive procedures, especially when there are repeated treatments.

SUMMARY

In one aspect, the present disclosure is directed to a microwave applicator. The microwave applicator includes a first transmission line segment, a second transmission line segment, and a third transmission line segment. The first transmission line segment includes a first inner conductor and a first outer conductor circumscribing the first inner conductor, the first outer conductor having a first outer diameter. The second transmission line segment includes a second inner conductor and a second outer conductor circumscribing the second inner conductor, the second outer conductor having a second outer diameter less than the first outer diameter. The third transmission line segment including a third inner conductor and a third outer conductor circumscribing the third inner conductor, the third outer conductor having a third outer diameter less than the second outer diameter.

One or more of the first transmission line segment, the second transmission line segment, the third transmission line segment is rigid, semi-rigid, or flexible. The diameter of the second and third inner conductors may be equal to the diameter of the first inner conductor. The second and third inner conductors may be an extension of the first inner conductor. The microwave applicator may also include a balun outer conductor circumscribing the third outer conductor. The outer diameter of the balun conductor may be equal to the outer diameter of the first outer conductor of the first transmission line segment.

In another aspect, the present disclosure features an antenna assembly that includes a coaxial cable including a first transmission line segment, a second transmission line segment, a third transmission line segment, and a coaxial balun disposed on the third transmission line segment. An outer diameter of the coaxial balun is equal to or approximately equal to an outer diameter of the first transmission line segment. The antenna assembly also includes radiating section formed at a distal end of the third transmission line segment, and a dielectric buffering and cooling segment configured to receive the coaxial cable and attached distal radiating section.

One or more of the first transmission line segment, the second transmission line segment, the third transmission line segment is rigid, semi-rigid, or flexible.

The dielectric buffering and cooling segment may include a first tube and a second tube disposed within the first tube. The second tube defines an outflow conduit between the inner surface of the first tube and the outer surface of the second tube, and defines an inflow conduit between the inner surface of the second tube and the outer surfaces of the coaxial cable and attached radiating section. The dielectric buffering and cooling segment may include a first tube defining inflow and outflow conduits for carrying cooling fluid.

BRIEF DESCRIPTION OF THE DRAWINGS

Objects and features of the presently disclosed energy-delivery devices with a fluid-cooled probe assembly and systems including the same will become apparent to those of ordinary skill in the art when descriptions of various embodiments thereof are read with reference to the accompanying drawings, of which.

DETAILED DESCRIPTION

This disclosure is generally directed to microwave ablation device capable of optimizing the power transfer from a generator to an antenna load while miniaturizing the cross section diameter of the microwave applicator. This is accomplished in part by matching the impedance of the generator and a first transmission line segment to the impedance looking into the network including second and third transmission line segments that terminate at the antenna.

According to the present disclosure, the diameter of the antenna geometry may be reduced to be less than or equal to the diameter of the coaxial feed-line. The miniaturization of the antenna geometry provides at least the following advantages: (1) it reduces the overall radial size of the microwave applicator without significantly compromising ablation performance or device strength; (2) it enables use of a larger coaxial cable feed-line, which reduces energy loss in the coaxial cable feed-line and thus increases energy delivery to the radiator; (3) it provides additional space within the microwave applicator without increasing overall radial size for various structures and features of the microwave applicator, such as the fluid channels, strengthening members, and centering features or sensors; and (4) it enables various manufacturing techniques, such as sliding the fully assembled microwave components into a multi-lumen catheter from one end, which would otherwise not be possible because of inconsistent radial dimensions between the microwave coaxial cable and the antenna.

With respect to endobronchial ablation, the miniaturization of the microwave applicator enables the technical feasibility (e.g., required tissue effect and appropriateness of the cooling) of a saline or water dielectric buffered and electrically choked (via the balun) microwave radiator at a 2.8 mm bronchoscope channel size. This further improves the tissue effect and cooling performance of the same application sized up to a 3.2 mm bronchoscope channel size device. Other intravascular, percutaneous, surgical, and laparoscopic applications where catheter size (French sizing) is of clinical significance are envisioned to benefit similarly. This may also provide space within the microwave applicator assemblies for thermocouple temperature sensors, which are described in U.S. application Ser. Nos. 13/836,519 and 13/924,277, the disclosure of each of which are incorporated by reference herein. Additionally, by maintaining a line-to-line dimension between the diameter of the feed-line coaxial segment and the diameter of the antenna geometry (including a balun), the microwave applicator assembly may be slid into a closed out (tipped) lumen from the proximal end, thus simplifying the manufacturing process. The manufacturing methods of the present disclosure may be used in the miniaturization and strengthening of ablation needles and catheters.

Embodiments of the microwave ablation systems and components are described with reference to the accompanying drawings. Like reference numerals may refer to similar or identical elements throughout the description of the figures. As shown in the drawings and as used in this description, the term "proximal" refers to that portion of the apparatus, or component of the apparatus, closer to the user and the term "distal" refers to that portion of the apparatus, or a component of the apparatus, farther from the user.

This description may use the phrases "in an embodiment," "in embodiments," "in some embodiments," or "in other embodiments," which may each refer to one or more of the same or different embodiments in accordance with the present disclosure.

As it is used in this description, "microwave" generally refers to electromagnetic waves in the frequency range of 300 megahertz (MHz) ($3\times10^8$ cycles/second) to 300 gigahertz (GHz) ($3\times10^{11}$ cycles/second). As it is used in this description, "ablation procedure" generally refers to any ablation procedure, such as, for example, microwave ablation, radiofrequency (RF) ablation, or microwave or RF ablation-assisted resection. As it is used in this description, "transmission line" generally refers to any transmission medium that can be used for the propagation of signals from one point to another. As it is used in this description, "fluid" generally refers to a liquid, a gas, or both.

Figure 1:
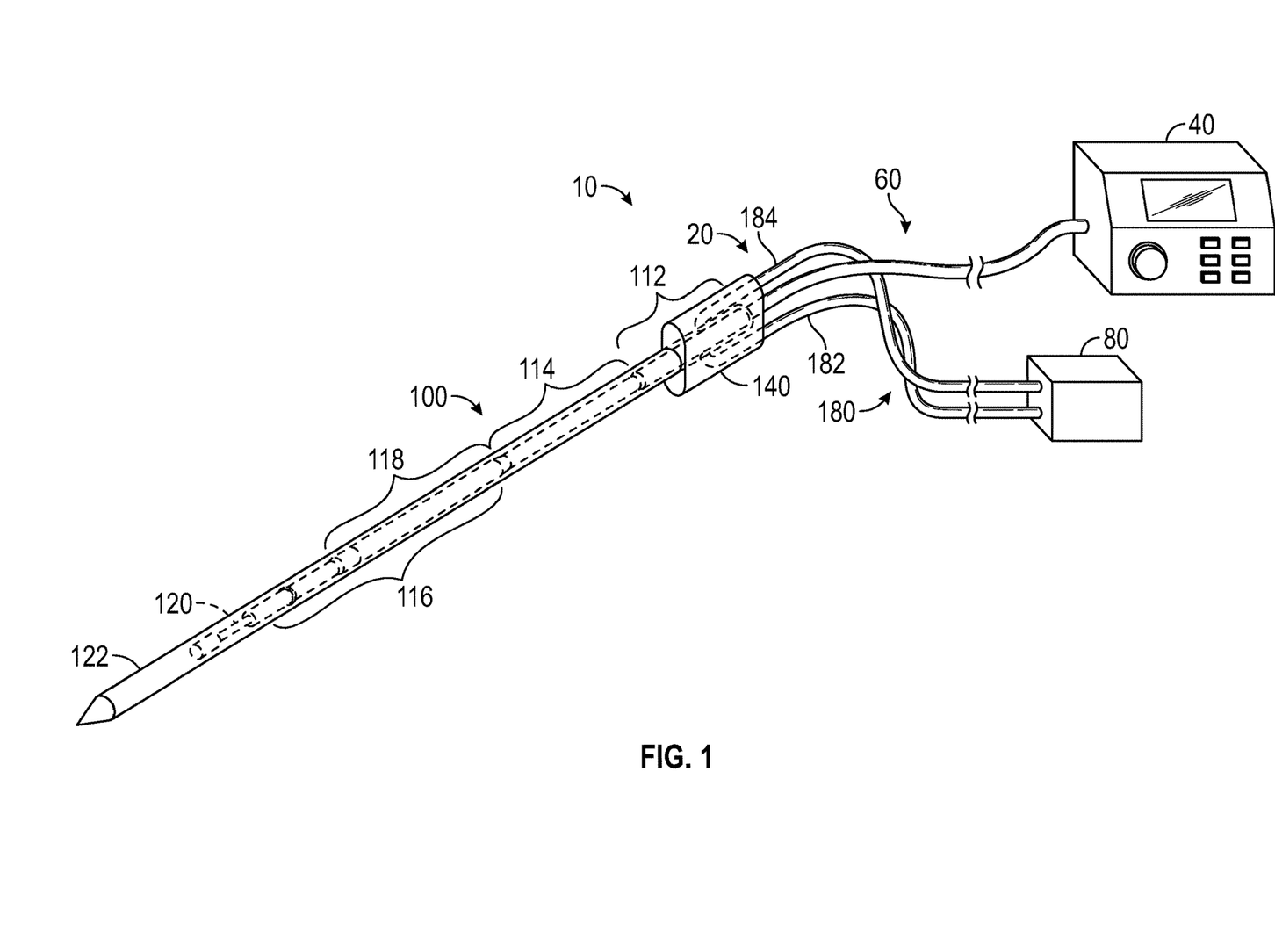
FIG. 1 is a block diagram of a microwave ablation system in accordance with aspects of the present disclosure.

FIG. 1 is a block diagram of a microwave tissue treatment system 10 in accordance with aspects of the present disclosure. The microwave tissue treatment system 10 includes a microwave tissue treatment device 20 having a microwave applicator or antenna assembly 100 connected to a microwave generator 40 through a feedline 60. The microwave tissue treatment device 20 may include one or more pumps 80, e.g., a peristaltic pump or the like, for circulating a cooling or heat dissipative fluid through the microwave applicator or antenna assembly 100 via an inflow fluid conduit 182 and an outflow fluid conduit 184 of a cooling system 180. The mechanical functionality of the pump in driving fluid through the system may be substituted by driving the fluid with pressurized and regulated reservoirs.

The feedline 60 may range in length from about 7 feet to about 10 feet, but may be either substantially longer or shorter if required in a particular application. The feedline 60 transfers microwave energy to microwave tissue treatment device 20. The feedline 60 includes a coaxial cable having an inner conductor, an outer conductor, and a dielectric interposed between the inner and outer conductors. The dielectric electrically separates and/or isolates the inner conductor from the outer conductor. The feedline 60 may further include any sleeve, tube, jacket, or the like formed of any conductive or non-conductive material. The feedline 60 may be separable from, and connectable to, the antenna assembly 100 or the microwave tissue treatment device 20.

The inner and outer conductors are each formed, at least in part, of a conductive material or metal, such as stainless steel, copper, or gold. In certain embodiments, the inner and outer conductors of feedline 60 may include a conductive or non-conductive substrate that is plated or coated with a suitable conductive material. The dielectric may be formed of a material having a dielectric value and tangential loss constant of sufficient value to electrically separate and/or isolate the respective inner and outer conductors from one another, including but not being limited to, expanded foam polytetrafluoroethylene (PTFE), polyamide, silicon dioxide, or fluoropolymer. The dielectric may be formed of any non-conductive material capable of maintaining the desired impedance value and electrical configuration between the respective inner and outer conductors. In addition, the dielectric may be formed from a combination of dielectric materials.

The antenna assembly 100 of the microwave tissue treatment system 10 includes a first transmission line segment 112, a second transmission line segment 114, a third transmission line segment 116 on which a choke or coaxial balun 118 is disposed, a distal radiating section 120, and a dielectric buffering and cooling structure 122.

The proximal portion of the antenna assembly 100 may include a connecting hub 140. The connecting hub 140 defines a conduit configured and dimensioned to receive a distal end of the feedline 60, additional conduits configured and dimensioned to receive the inflow conduit 182 and the outflow conduit 184 of the cooling system 180, and one or more apertures formed in an internal surface of the connecting hub 140 that are configured and dimensioned to receive the inflow conduit 182 and the outflow conduit 184, respectively. Connecting hub 140 may be formed of any suitable material including, but not limited to, polymeric materials. Although not explicitly shown, the hub may also include conduits configured and dimensioned to receive sensors, including but not limited to thermocouples or impedance monitoring electrodes, and may house one or more components of a radiometer used to sense the effects of ablation on the emissions of tissue.

As described above, the antenna assembly 100 of the present disclosure minimizes the radial dimension of a microwave applicator 200. Specifically the radial dimensions of the metallic structure of the microwave applicator 200 are optimized to match the impedance of the generator and first transmission line section 112 with the second and third transmission line sections 114 and 116, respectively, as will be described below with reference to FIGS. 2-5.

Figure 2:
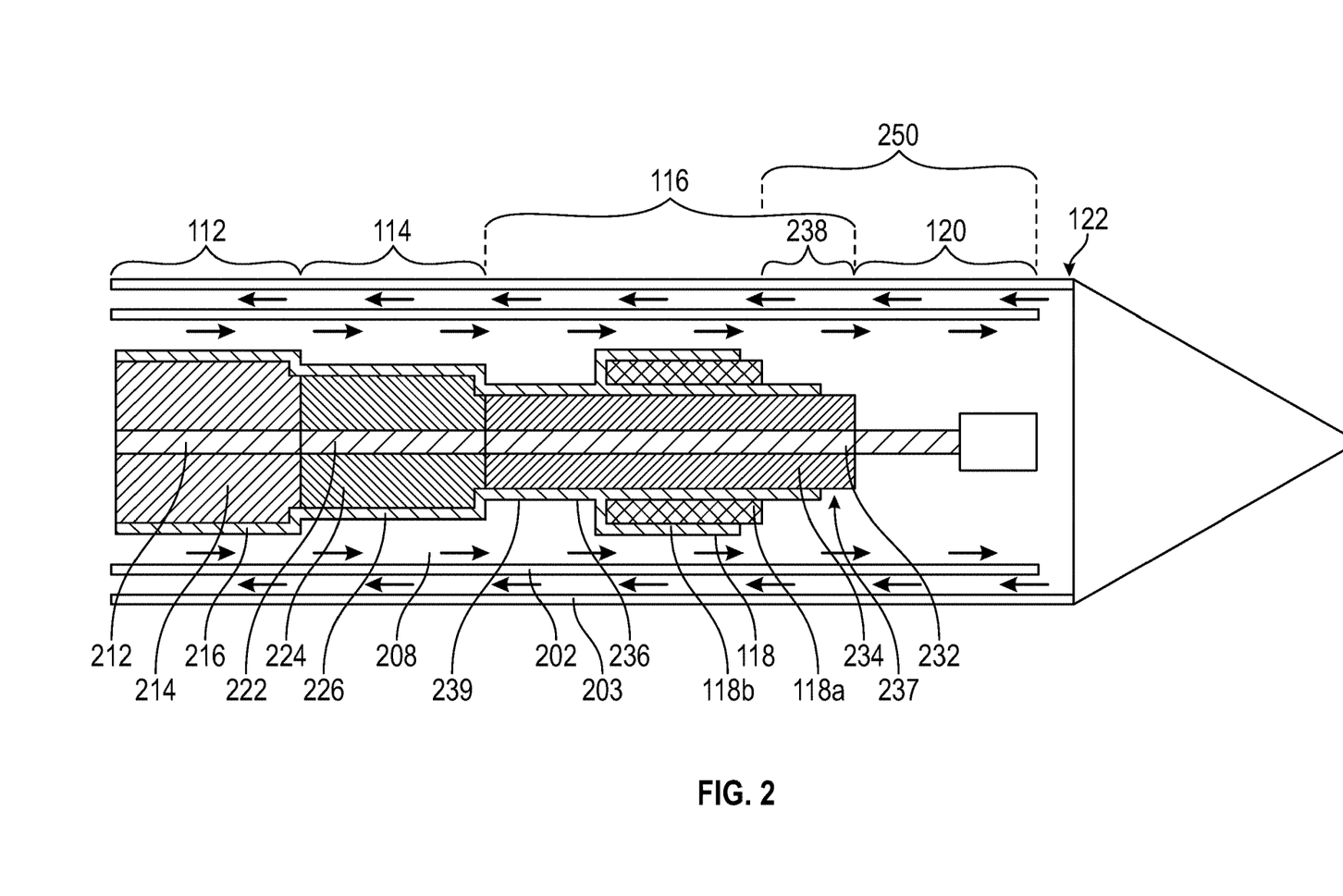
FIG. 2 is a side view of a microwave applicator of the microwave ablation system of FIG. 1 in accordance with aspects of the present disclosure.
Figure 3A:
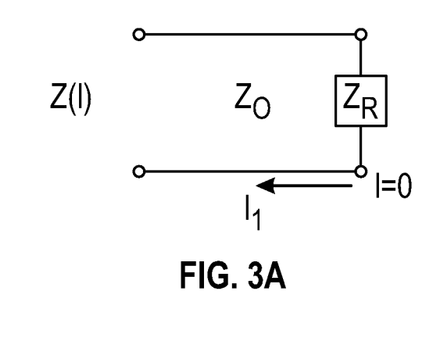
FIG. 3 is a transmission line network representation of the microwave applicator of FIG. 2.
Figure 3B:
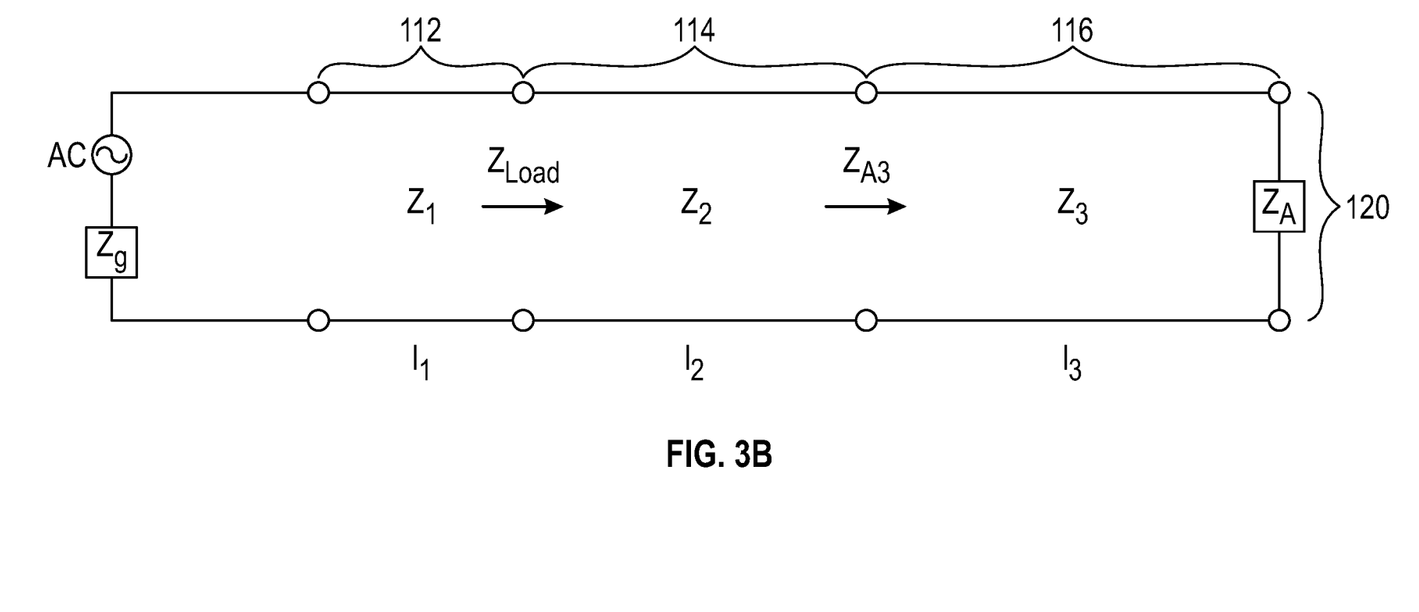
Figure 4A:
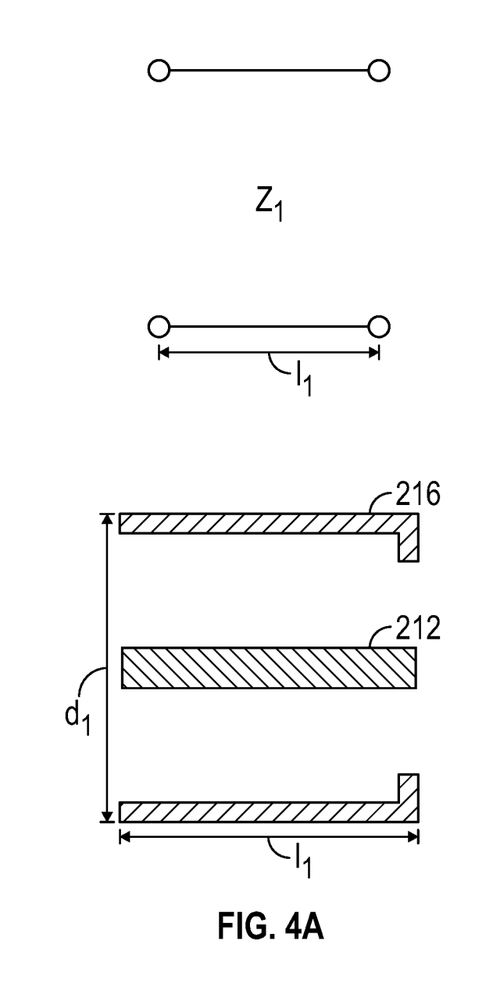
FIG. 4A is a schematic representation of a first transmission line section of the microwave applicator of FIG. 2.
Figure 4B:
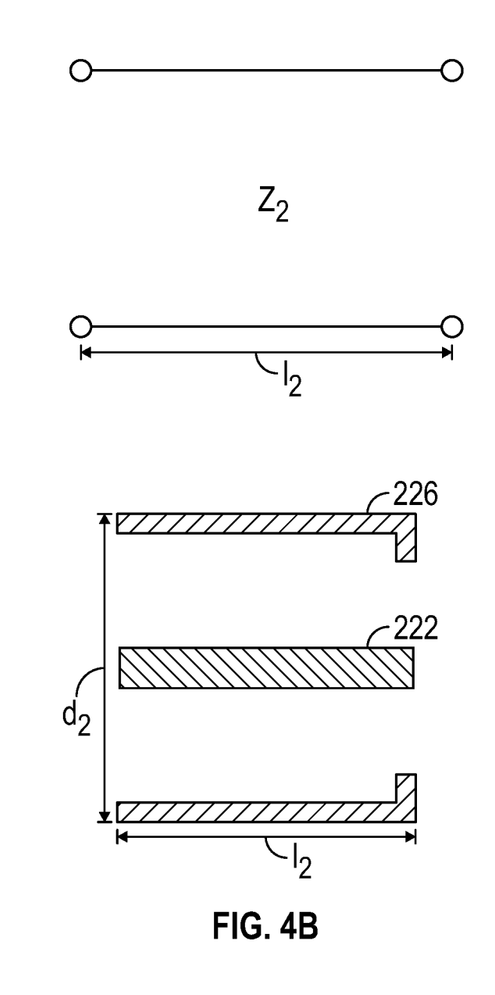
FIG. 4B is a schematic representation of a second transmission line section of the microwave applicator of FIG. 2.
Figure 4C:
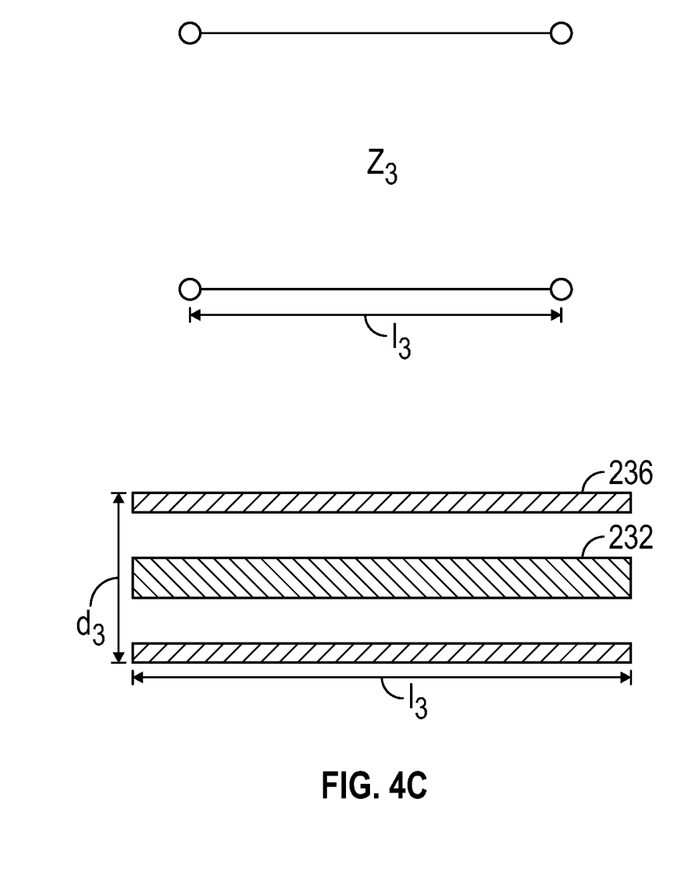
FIG. 4C is a schematic representation of a third transmission line section of the microwave applicator of FIG. 2.
Figure 4D:
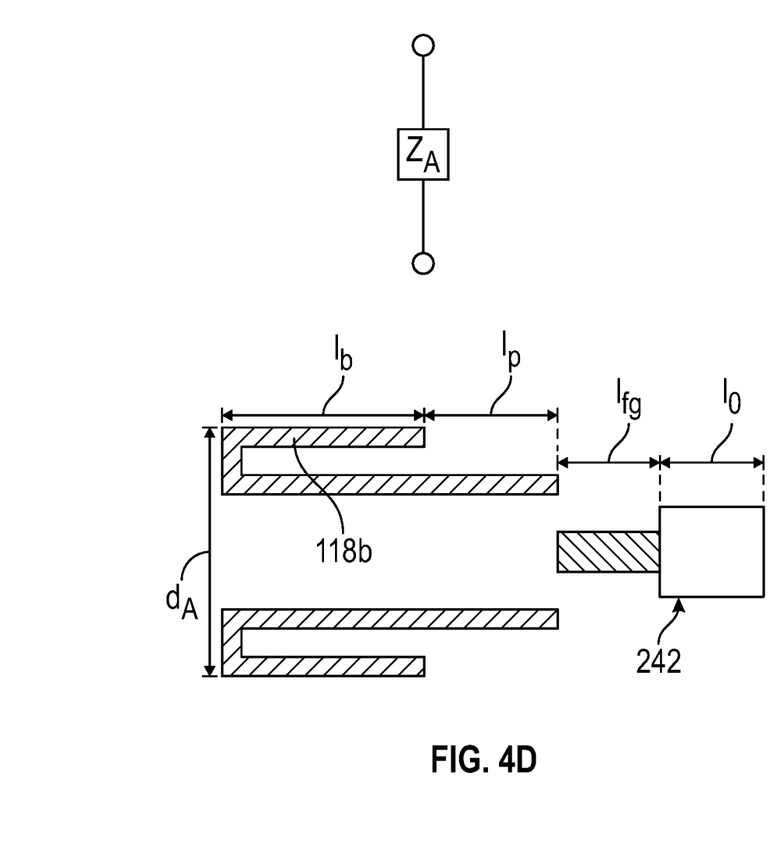
FIG. 4D is a schematic representation of a distal radiating section of the microwave applicator of FIG. 2.
Figure 5:
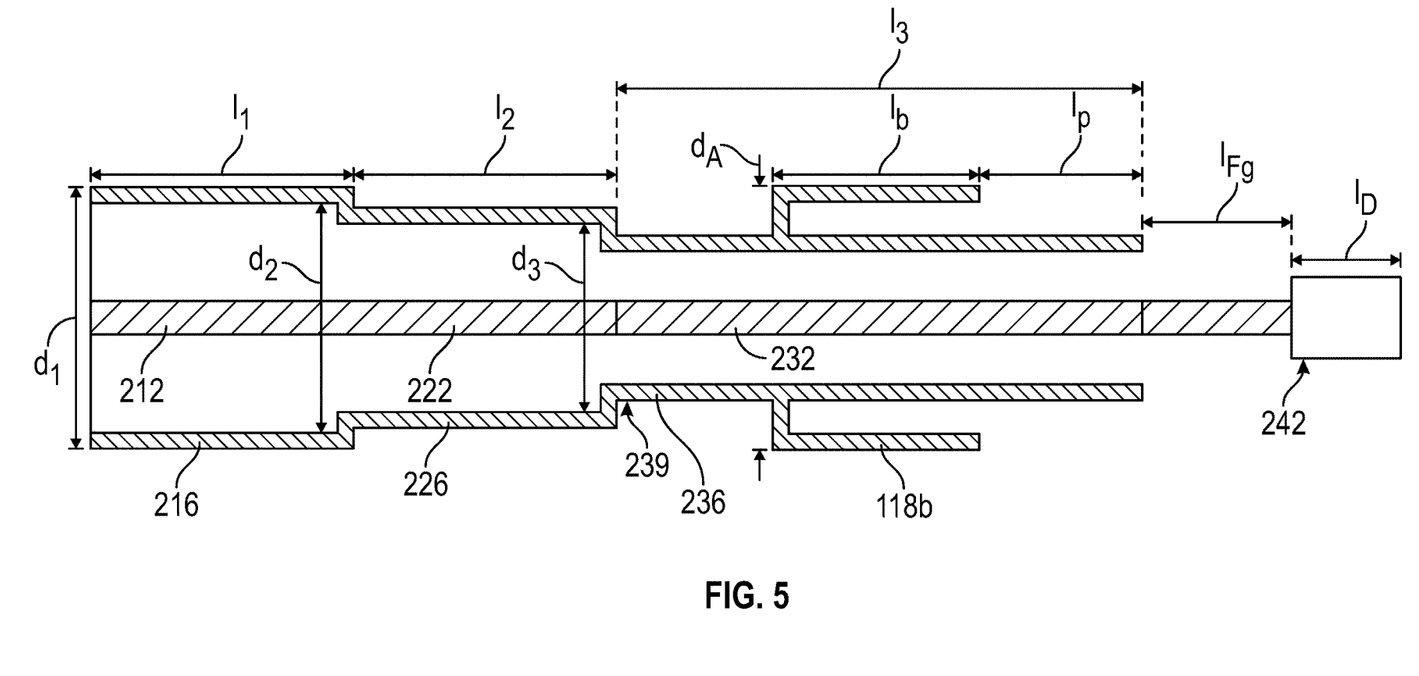
FIG. 5 is a combined schematic representation of FIGS. 4A-4D.

FIG. 2 shows the microwave applicator 200 inserted into the dielectric buffering and cooling structure 122. The first transmission line segment 112 (FIG. 1) may be constructed of a coaxial cable of any variety, including a rigid, semi-rigid, or flexible coaxial cable. The impedance of the waveguide formed by the coaxial cable may be 50 ohms, but may range from 20 ohms to 150 ohms. An inner conductor 212 of the first transmission line section segment 112 is surrounded by a dielectric insulator 214, which, in turn, is partially or fully covered by an outer conductor 216 (also referred to as a shield).

The inner conductor 212 may be a silver-plated solid copper wire. The dielectric insulator 214 may be a dielectric tape, an extruded polytetrafluoroethylene (PTFE) dielectric insulator, wrapped PTFE, foamed PTFE, or perfluoroalkoxy (PFA). The outer conductor 216 may be a silver-plated copper wire braid constructed from either flat or round braid wire. A jacket (not shown) for environmental and mechanical robustness may be applied onto or melted into the braided shield. The jacket may be a heat shrink material, such as polyethylene terephthalate (PET) or fluorinated ethylene propylene (FEP), or an extruded thermoplastic. The first transmission line segment 112 has an outer radial dimension $d_1$ (See FIG. 5).

The second transmission line segment 114 may include an inner conductor 222 that is the same as the inner conductor 212 of the coaxial feed-line segment 112. Thus, the inner conductor 222 may be unchanged and seamless between the first transmission line segment 112 and the second transmission line segment 114 to simplify manufacture of the microwave applicator and improve electrical performance. In other words, the inner conductor 222 may be an extension of the inner conductor 212. In embodiments, the radial dimension of the inner conductor 222 may be reduced. The difference between the first transmission line segment 112 and the second transmission line segment 114 is that the outer radial dimension of the second transmission line segment 114 $d_2$ is reduced by employing a dielectric insulator 224 having a reduced diameter as compared to dielectric insulator 214 of the first transmission line segment.

The length of the second transmission line segment 114 may be optimized for electrical performance at one quarter of the wavelength of the frequency of operation. The length of the second transmission line segment 114 may be scaled by the dielectric constant of the second transmission line segment's dielectric insulator 224. For example, the length of the second transmission line segment 114 may be 2.1 cm for an operation frequency of 2450 MHz. In other embodiments, the length of the second transmission line segment 114 may deviate from a quarter wavelength. For example, the length of the second transmission line segment 114 may be 5.6 cm for an operation frequency of 915 MHz and 0.9 cm for 5800 MHz. In yet other embodiments, the second transmission line segment 114 may be stepped down using a variety of approaches including a taper step down, a multiple segment step down, or an exponential tapering.

The second transmission line segment 114 may be constructed from the same materials as the first transmission line segment 112, or the second transmission line segment 114 may use a different combination of materials than the first transmission line segment 112. The dielectric insulator 224 may be a foamed PTFE, such as low-density PTFE (LDPTFE) or microporous PTFE, tape-wrapped PTFE, tape-wrapped and sintered PTFE, or PFA. The outer conductor 226 may be a silver-plated copper flat wire braid, a solid-drawn copper tube, a conductive ink-coated PET heat shrink (e.g., silver ink-coated PET heat shrink), or a silver-plated copper-clad steel braid.

The third transmission line segment 116 may include an inner conductor 232 that is unchanged and seamless with the inner conductor 222 of the second transmission line segment 114 and the inner conductor 212 of the first transmission line segment 112, which would simplify manufacture of the third transmission line segment 116 and would improve electrical performance. If the inner conductor 232 of the third transmission line segment 116 were to change with the third transmission line segment 116, its radial dimension may be reduced. A difference between the third transmission line segment 116 and the second transmission line segment 114 is that the outer radial dimension of the third transmission line segment 116 $d_3$ is reduced again by employing a dielectric insulator 234 having a reduced diameter as compared to dielectric insulator 214 of the first transmission line segment 112 and dielectric insulator 224 of the second transmission line segment 114.

The third transmission line segment 116 may be constructed from the same materials as or different materials from the first transmission line segment 112 and/or the second transmission line segment 114. The dielectric insulator 234 of the radiator base segment 116 may be a low-density PTFE (e.g., a foamed PTFE), a tape-wrapped PTFE, a tape-wrapped and sintered PTFE, or a PFA. The outer conductor 236 may be a silver-plated copper flat-wire braid, a solid-drawn copper tube, a silver ink-coated PET heat shrink, or a silver-plated copper-clad steel braid.

The coaxial balun 118 is assembled on top of the third transmission line segment 116 as shown in FIG. 2. The coaxial balun 118 is composed of a balun dielectric insulator 118a and a balun outer conductor 118b. The balun dielectric insulator 118a may extend beyond the distal end of the balun outer conductor 118b.

The overall outer diameter of the coaxial balun 118 $d_A$ may be set equal to or less than the overall outer diameter of the first transmission line segment 112, such that the largest overall radial dimension of the device is not increased by the coaxial balun 118. The coaxial balun 118 may be constructed from the same materials as the first transmission line segment 112, or may vary from the specific materials of the first transmission line segment 112.

The third transmission line segment 116 includes a feed gap 237 formed by the exposing of the dielectric insulator 234 and the removal of the distal most portion of the outer conductor 236. The portion of the outer conductor 236 extending beyond the distal end of the balun 118, and extending to the feed gap 237 forms a proximal radiating section 238. Distal of the feed gap 237, a he distal radiating section 120 includes an elongated conductor 242 which is soldered, crimped, or welded onto the distal end of the inner conductor 232 of the third transmission line segment 116 and may abut against the distal end of the feed gap 237 formed from the dielectric insulator 234. In combination the proximal and distal radiating sections 238 and 120 form radiator 250. The shape of the elongated conductor 242 may be a cylinder. Alternatively, the distal radiating section 120 may be composed of several cylinders of varying diameter, such as a barbell or pin with a widened base. Additional heat-sinking features, such as burs and fins, may be added to the elongated conductor 242 to increase the radiating effectiveness of the microwave applicator 200. These features, such as the barbell mentioned above, may also help to center the radiator within the dielectric buffering and cooling structure 122.

The radiator 250 may be constructed from the same materials as or different materials from the first transmission line segment 112, the second transmission line segment 114, and/or the third transmission line segment 116.

The dielectric buffering and cooling structure 122 includes a mechanical support for the device, circulated cooling fluid, such as gas or liquid, and chambers to enable the circulation of the fluid, such as concentric inflow and outflow tubes 202 and 203 forming fluid paths 208 and 206, respectively. The dielectric buffering of the antenna from the surrounding tissue environment is provided by the circulated liquid extending over the length of the radiating section. Alternatively, the cooling lumens and fluids may terminate proximal to the distal radiating section 120 and high dielectric solid material may be disposed distally over the radiating section 120 of the microwave applicator to dielectrically buffer the antenna and provide mechanical stiffness.

The dielectric buffering and cooling structure 122 may be composed of various thermoplastics and may be manufactured according to a multi-lumen extrusion approach. The dielectric buffering and cooling structure 122 may include an outflow tube 203 composed of fiber glass and an inflow tube 202 composed of polyimide or PET extrusion and may be manufactured according to a concentric approach, in which materials are layered upon each other. The inflow tube 202 and the outflow tube 203 may alternatively be composed of a Kevlar braid thermoplastic composite. The cooling fluid may be water, saline, or any common water-based liquid. The high dielectric solid material may be a ceramic material, such as YTZP.

In order to maximize the power transfer from the generator to the antenna assembly/tissue, the impedance $Z_{LOAD}$, which is the impedance at the junction of the first transmission line segment 112 and the second transmission line segment 114, should be substantially equal to the generator impedance $Z_G$. The design of the microwave applicator 200 capable of achieving the maximum power transfer will be discussed below with reference to the schematic representations shown in FIGS. 3 through 5. The impedance of a transmission line is calculated as follows:

$$Z(l) = Z_0 \frac{Z_L + jZ_0 \tan \frac{2\pi l}{\lambda}}{Z_0 + jZ_L \tan \frac{2\pi l}{\lambda}}, \quad (1)$$

where $Z_0$ is the impedance of the transmission line, l is the length of the line, and $Z_L$ is the impedance of the load terminating the line. In situations where the length of the line l is equal to a quarter wavelength, the impedance of the transmission line is calculated as follows:

$$Z\left(\frac{\lambda}{4}\right) = \frac{Z_0^2}{Z_L}. \quad (2)$$

Impedance $Z_A$ of the distal radiating section 120 is optimized for spherical ablation in tissue and the first transmission line segment 112 is designed to have impedance $Z_1$ that is equal to the impedance $Z_G$ of the generator.

Starting with the junction between the third transmission line segment 116 and the distal radiating section 120, the impedance $Z_{A3}$ is calculated using equation (1) as follows:

$$Z_{A3} = Z_3 \frac{Z_A + jZ_3 \tan \frac{2\pi l_3}{\lambda}}{Z_3 + jZ_A \tan \frac{2\pi l_3}{\lambda}}. \quad (3)$$

Using equations (1) and (3) above, the impedance $Z_{LOAD}$ at the junction of the first transmission line segment 112 and the second transmission line segment 114 is calculated as follows:

$$Z_{LOAD} = Z_2 \frac{Z_{A3} + jZ_2 \tan \frac{2\pi l_2}{\lambda}}{Z_2 + jZ_{A3} \tan \frac{2\pi l_2}{\lambda}}. \quad (4)$$

By setting the length $l_2$ of the second transmission line segment 114 to a quarter wavelength, the impedance $Z_{LOAD}$ is calculated using equation (2) as follows:

$$Z_{LOAD} = \frac{Z_2^2}{Z_{A3}}, \text{ where } l_2 \text{ equals } \lambda/4. \quad (5)$$

Then equation (3) is substituted into equation (5) and the impedance $Z_{LOAD}$ is calculated as follows:

$$Z_{LOAD} = \frac{Z_2^2}{Z_3} \frac{Z_3 + jZ_A \tan \frac{2\pi l_3}{\lambda}}{Z_A + jZ_3 \tan \frac{2\pi l_3}{\lambda}}. \quad (6)$$

The impedance of the second transmission line section 114 is calculated by solving equation (6) for $Z_2$ as follows:

$$Z_2 = \sqrt{Z_{LOAD} Z_3 \frac{Z_A + jZ_3 \tan \frac{2\pi l_3}{\lambda}}{Z_3 + jZ_A \tan \frac{2\pi l_3}{\lambda}}}. \quad (7)$$

Equation (7) can be simplified as follows:

$$Z_2 = \sqrt{C_3 \frac{C_A + jC_3 \tan C_\lambda l_3}{C_3 + jC_A \tan C_\lambda l_3}}. \quad (8)$$

Thus, in order to optimize the match between the generator and the microwave applicator the length $l_3$ of the third transmission line segment is adjusted where the length $l_3$ is greater than a quarter wavelength of the microwave energy due to the presence of the balun 116 and an antenna proximal arm 239 (FIG. 2). Adjusting the length of $l_3$ adjust the impedance $Z_2$ of the second transmission line section 114. The impedance $Z_2$ of the second transmission line segment 114 is selected to range between the impedance $Z_1$ of the first transmission line segment 112 and the impedance $Z_3$ of the third transmission line segment 116. The impedances of the first, second, and third transmission line segments 112, 114 and 116 are based on the processing techniques and the materials used to construct the segments.

Although embodiments have been described in detail with reference to the accompanying drawings for the purpose of illustration and description, it is to be understood that the inventive processes and apparatus are not to be construed as limited thereby. It will be apparent to those of ordinary skill in the art that various modifications to the foregoing embodiments may be made without departing from the scope of the disclosure.

What is claimed is:

1. A microwave antenna assembly, comprising:
a first transmission line segment including a first inner conductor and a first outer conductor surrounding the first inner conductor;
a second transmission line segment including a second inner conductor and a second outer conductor surrounding the second inner conductor, the second outer conductor having an outer diameter less than an outer diameter of the first outer conductor;
a third transmission line segment including a third inner conductor, a third outer conductor surrounding the third inner conductor, and a dielectric material disposed between the third inner conductor and the third outer conductor, the dielectric material extending distally beyond a distal end of the third outer conductor, wherein an impedance of the second transmission line segment is based on a length of the third transmission line segment; and
a balun surrounding the third outer conductor and having an outer diameter equal to an outer diameter of the first outer conductor.

2. The microwave antenna assembly according to claim 1, wherein a diameter of the first inner conductor is equal to a diameter of at least one of the second inner conductor or the third inner conductor.

3. The microwave antenna assembly according to claim 1, wherein the second inner conductor extends distally from a distal end of the first inner conductor, and the third inner conductor extends distally from a distal end of the second inner conductor.

4. The microwave antenna assembly according to claim 1, wherein the balun includes a balun dielectric insulator disposed on the third outer conductor and a balun outer conductor electrically coupled to the third outer conductor and surrounding the balun dielectric insulator.

5. The microwave antenna assembly according to claim 4, wherein an outer diameter of the balun outer conductor is equal to the outer diameter of the first outer conductor.

6. The microwave antenna assembly according to claim 1, wherein the length of the third transmission line segment is determined based on a wavelength of microwave energy transmitted through the microwave antenna assembly.

7. The microwave antenna assembly according to claim 1, wherein the microwave antenna assembly is configured to couple to a generator having a generator impedance $Z_G$.

8. The microwave antenna assembly according to claim 7, wherein a junction of the first transmission line segment and the second transmission line segment includes a junction impedance $Z_{load}$ that is matched to the generator impedance $Z_G$ by the length of the third transmission line segment.

9. The microwave antenna assembly according to claim 1, wherein an outer diameter of the third outer conductor is less than the outer diameter of the second outer conductor.

10. An antenna assembly, comprising:
a coaxial cable having an inner conductor and an outer conductor coaxially surrounding the inner conductor, the coaxial cable including:
a first transmission line segment;
a second transmission line segment;

a third transmission line segment having a distal radiating section configured to deliver energy to tissue; and a coaxial balun surrounding the third transmission line segment; and a dielectric tube surrounding at least a portion of the third transmission line segment to define a fluid path between the dielectric tube and the third transmission line, the fluid path configured to receive cooling fluid for cooling the distal radiating section, wherein a distal end of the dielectric tube is disposed distal to a distal end of the outer conductor.

11. The antenna assembly according to claim 10, wherein the coaxial cable has a maximum outer diameter equal to an outer diameter of the coaxial balun and an outer diameter of the first transmission line.

12. The antenna assembly according to claim 10, wherein the dielectric tube has a diameter greater than a maximum outer diameter of the coaxial cable.

13. The antenna assembly according to claim 10, wherein the third transmission line segment has an outer diameter smaller than an outer diameter of the first transmission line segment.

14. The antenna assembly according to claim 10, wherein an outer diameter of the coaxial balun is equal to an outer diameter of the first transmission line segment.

15. The antenna assembly according to claim 10, further comprising a junction impedance $Z_{load}$ at a junction of the first transmission line segment and the second transmission line segment, wherein a length of the third transmission line segment is greater than a quarter wavelength and matches the junction impedance $Z_{load}$ to a generator impedance $Z_G$ of a generator coupled to the antenna assembly.

16. A microwave antenna assembly, comprising:
a first transmission line segment including a first inner conductor and a first outer conductor surrounding the first inner conductor;

a second transmission line segment including a second inner conductor and a second outer conductor surrounding the second inner conductor;

a third transmission line segment including a third inner conductor, a third outer conductor surrounding the third inner conductor, and a dielectric material disposed between the third inner conductor and the third outer conductor; and an inner dielectric tube surrounding at least a portion of the third transmission line segment to define a first fluid path between the inner dielectric tube and the third transmission line, wherein a distal end of the inner dielectric tube is disposed distal to a distal end of the third outer conductor.

17. The microwave antenna assembly according to claim 16, wherein the second outer conductor has an outer diameter less than an outer diameter of the first outer conductor.

18. The microwave antenna assembly according to claim 16, wherein an impedance of the second transmission line segment is based on a length of the third transmission line segment.

19. The microwave antenna assembly according to claim 16, further comprising
an outer dielectric tube surrounding at least a portion of the inner dielectric tube to define a second fluid path between the outer dielectric tube and the inner dielectric tube, the second fluid path in fluid communication with the first fluid path.

* * * * *